United States Patent [19]
Terlau et al.

[11] Patent Number: 5,672,682
[45] Date of Patent: Sep. 30, 1997

[54] CONOTOXIN PEPTIDE PVIIA

[75] Inventors: Heinrich Terlau, Göttingen, Germany; Ki-Joon Shon, Salt Lake City, Utah; Michelle Grilley, Salt Lake City, Utah; Baldomero M. Olivera, Salt Lake City, Utah

[73] Assignee: University of Utah Research Foundation, Salt Lake City, Utah

[21] Appl. No.: 619,936

[22] Filed: Mar. 18, 1996

[51] Int. Cl.$^6$ .......................... C07K 14/00; C07K 14/435
[52] U.S. Cl. .......................... 530/324; 530/300; 530/321
[58] Field of Search .................................. 530/300, 317, 530/324; 514/2, 9, 12

[56] References Cited

U.S. PATENT DOCUMENTS

| | | | |
|---|---|---|---|
| 4,447,356 | 5/1984 | Olivera et al. | 530/327 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,424,218 | 6/1995 | Miljanich et al. | 436/503 |
| 5,432,155 | 7/1995 | Olivera et al. | 514/12 |
| 5,514,774 | 5/1996 | Olivera et al. | 530/324 |
| 5,589,340 | 12/1996 | Olivera et al. | 435/6 |

FOREIGN PATENT DOCUMENTS

| | | |
|---|---|---|
| WO 93/10145 | 5/1993 | WIPO . |
| WO 93/13128 | 7/1993 | WIPO . |
| WO 95/11256 | 4/1995 | WIPO . |

OTHER PUBLICATIONS

Colledge, C.J. et al. (1992). "Precursor Structure of ω–Conotoxin GVIA Determined from a cDNA Clone, " *Toxicon* 30:1111–1116.

Cruz, L.J. and Olivera, B.M. (1986). "Calcium Channel Antagonist. ω–Conotoxin Defines a New High Affinity Site," *J. Biol. Chem.* 261:6230–6233.

Dudley, S.C. et al. (1995). "A μ–Conotoxin–Insensitive Na$^+$ Channel Mutant: Possible Localization of a Binding Site at the Outer Vestibule," *Biophysical J.* 69:1657–1665.

Fainzilber, M. et al. (1991). "Mollusc–specific toxins from the venom of *Conus textile neovicarius*, " *Eur. J. Biochem.* 202:589–595.

Fainzilber, M. et al. (1994). "A New Neurotoxin Receptor Site on Sodium Channels Is Identified by a Conotoxin That Affects Sodium Channel Inactivation in Molluscs and Acts as an Antagonist in Rat Brain," *J. Biol. Chem.* 269:2574–2580.

Fainzilber, M. et al. (1994). "New Mollusc–Specific α–Conotoxins Block Aplysia Neuronal Acetylcholine Receptors," *Biochemistry*, 33:9523–9529.

Gray, W.R. et al. (1981). "Peptide Toxins from *Conus geographus* Venom," *J. Biol. Chem.* 256:4734–4740.

Hasson, A. et al. (1993), "Alteration of Sodium Currents by New Peptide Toxins From the Venom of a Molluscivorous Conus Snail," *Eur. J. Neurosci.* 5:56–64.

Hillyard, D.R. et al. (1989). "A Molluscivorous Conus Toxin: Conserved Frameworks in Conotoxins," *Biochemistry* 28:358–361.

Hillyard, D.R. et al. (1992). "A New Conus Peptide Ligand for Mammalian Presynaptic Ca$^{2+}$Channels," *Neuron* 9:69–77.

Hopkins, C. et al. (1995). "A New Family of Conus Peptides Targeted to the Nicotinic Acetylcholine Receptor," *J. Biol. Chem.* 270:22361–22367.

Kobayashi, J. et al. (1982). "Isolation of a Cardiotonic Glycoprotein, Striatoxin, from the Venom of the Marine Snail *Conus Striatus*," *Biochem. Biophys. Res. Comm.* 105:1389–1395.

Lundy, P.M. et al. (1991). "Pharmacological evidence form an ω–conotoxin dihydropyridine–insensitive neuronal Ca$^{2+}$ channel," *Eur. J. Pharmacol.* 206:61–68.

McCleskey, E.W. et al. (1987). "ω–Conotoxin: Direct and persistent blockade of specific types of calcium channels in neurons but not muscle," *Proc. Natl. Acad. Sci. USA* 84:4327–4331.

McIntosh, M. et al. (1982). "Isolation and Structure of a Peptide Toxin from the Marine Snail *Conus magus*," *Arch. Biochem. Biophys.* 218:329–334.

McIntosh, J.M. et al. (1995). "A New Family of Conotoxins That Blocks Voltage–gated Sodium Channels," *J. Biol. Chem.* 270:16796–16802.

Monje, V.D. et al. (1993). "A New Conus Peptide Ligand For Ca Channel Subtypes," *Neuropharmacology* 32:1141–1149.

Myers, R.A. et al. (1993). "Conus Peptides as Chemical Probes for Receptors and Ion Channels," *Chem. Rev.* 93:1923–1936.

Olivera, B.M. et al. (1984). "Purification and Sequence of a Presynaptic Peptide Toxin from *Conus geographus* Venom," *Biochemistry* 23:5087–5090.

Olivera, B.M. et al. (1985). "Peptide Neurotoxins from Fish–Hunting Cone Snails," *Science* 230:1338–1343.

(List continued on next page.)

Primary Examiner—Marianne P. Allen
Assistant Examiner—Patricia A. Duffy
Attorney, Agent, or Firm—Venable, Baetjer, Howard & Civiletti, LLP

[57] ABSTRACT

A new peptide, κ-conotoxin PVIIA, is disclosed. This peptide is found naturally in the cone snail Conus purpurascens and has the amino acid sequence Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO:1) where Xaa represents 4-trans-hydroxyproline hydroxyproline or proline. This peptide together with a previously disclosed peptide, δ-conotoxin PVIA, act synergistically to rapidly immobilize fish which are injected with the two peptides. Injection of κ-conotoxin PVIIA alone results in different symptoms with an injected fish becoming hyperactive and then contracting and suddenly extending all major fins. This "fin-popping" occurs repeatedly resulting in a series of jerky movements, but injection of only κ-conotoxin PVIIA does not immobilize or kill the fish.

3 Claims, 5 Drawing Sheets

OTHER PUBLICATIONS

Olivera, B.M. et al. (1987). "Neuronal calcium Channel Antagonists. Discrimination between Calcium Channel Subtypes Using ω–Conotoxin from *Conus magus* Venom," *Biochemistry* 26:2086–2090.

Olivera, B.M. et al. (1990). "Diversity of Conus Neuropeptides," *Science* 249:257–263.

Olivera, B.M. et al. (1991). "Conotoxins," *J. Biol. Chem.* 266:22067–22070.

Ramilo, C.A. et al. (1992). "Novel α–and ω–Conotoxins from Conus striatus Venom," *Biochemistry* 31:9919–9926.

Regan, L.J. et al. (1991). "Ca2+ Channels in Rat Central and Peripheral Neurons: High–Threshold Current Resistant to Dihydropyridine Blockers and ω–Conotoxin," *Neuron* 6:269–280.

Rivier, J. et al. (1987). "Neuronal Calcium Channel Inhibitors. Synthesis of ω–Conotoxin GVIA and Effects on $^{45}$Ca Uptake by Synaptosomes," *J. Biol. Chem.* 262:1194–1198.

Shon, K–J. et al. (1994). "δ–Conotoxin GmVIA, a Novel Peptide from the Venom of *Conus gloriamaris*," *Biochemistry* 33:11420–11425.

Shon, K–J. et al. (1995). "Purification, Characterization, Synthesis, and Cloning of the Lockjaw Peptide from *Conus purpurascens* Venom," *Biochemistry* 34:4913–4918.

Spira, M.E. et al. (1993). "Chemical and Electrophysiological Characterization of New Peptide Neurotoxins from the Venom of the Molluscivorous Snail *Conus textile neovicarius*: A Review," *Isr. J. Med. Sci.* 29:530–543.

Woodward, S.R. et al. (1990). "Constant and hypervariable regions in conotoxin propeptides," *EMBO J.* 9:1015–1020.

Yoshikami, D. et al. (1989). "The Inhibitory Effects of Omega–Conotoxins on Ca Channels and Synapses," *Ann. N.Y. Acad. Sci.* 560:230–248.

Teralu et al (1996). "Strategy For Rapid Immobilization of Prey by a Fish–Hunting Marine Snail," *Nature* 381:148–151.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO -continued

```
( v i ) ORIGINAL SOURCE:
        ( A ) ORGANISM: Conus purpurascens ( i x ) FEATURE:
        ( A ) NAME/KEY: Modified-site
        ( B ) LOCATION: 4
        ( D ) OTHER INFORMATION: /product="4Hyp"
              / note= "Amino acid 4 may be 4-trans-hydroxyproline."

( i x ) FEATURE:
        ( A ) NAME/KEY: Disulfide-bond
        ( B ) LOCATION: 1..16

( i x ) FEATURE:
        ( A ) NAME/KEY: Disulfide-bond
        ( B ) LOCATION: 8..20

( i x ) FEATURE:
        ( A ) NAME/KEY: Disulfide-bond
        ( B ) LOCATION: 15..26

( x i ) SEQUENCE DESCRIPTION: SEQ ID NO:1:

Cys  Arg  Ile  Xaa  Asn  Gln  Lys  Cys  Phe  Gln  His  Leu  Asp  Asp  Cys  Cys
1                  5                           10                          15

Ser  Arg  Lys  Cys  Asn  Arg  Phe  Asn  Lys  Cys  Val
               20                      25
```

CONOTOXIN PEPTIDE PVIIA

This invention was made with Government support under Grant No. PO1 GM 28677 from the National Institute of General Medical Sciences of the National Institutes of Health, Bethesda, Md. The United States Government has certain rights in the invention.

BACKGROUND OF THE INVENTION

This invention relates to a peptide of 27 amino acid residues. This peptide is naturally available in minute amounts in the venom of the cone snail *Conus purpurascens* and it may also be synthesized. This peptide includes three cyclizing disulfide linkages.

The publications and other materials used herein to illuminate the background of the invention, and in particular, cases to provide additional details respecting the practice, are incorporated by reference, and for convenience are referenced in the following text by author and are listed alphabetically by author in the appended bibliography.

For a predatory animal to use venom to capture prey requires many adaptations, including a system for venom production as well as an apparatus to deliver the venom. Some venomous animals immobilize their prey with remarkable efficiency and speed. Analysis of venoms made by different animals to capture prey reveals that their components have a wide variety of physiological targets. A unifying conceptual overview that rationalizes the diverse molecular mechanisms of toxins in venoms needs to be developed.

In terms of mechanistic sophistication, the fish-hunting geography cone snail, *Conus geographus* would seem noteworthy (Olivera et al., 1990; Myers et al., 1993). Its venom inhibits not only transmitter release from the presynaptic nerve ending, but reception of the neurotransmitter as well as generation of action potentials in skeletal muscles of prey. The venom components responsible are the ω-conotoxins (blockers of presynaptic voltage-gated calcium channels), the α-conotoxins (inhibitors of skeletal muscle nicotinic acetylcholine receptor) and the μ-conotoxins (blockers of voltage-gated sodium channels in the plasma membrane of muscle fibers); all are small disulfide-rich peptides (13–27 amino acids). These three groups of neurotoxins act synergistically to block neuromuscular transmission. (Olivera et al., 1985) However, even with the "triple-threat" afforded by these toxins, it still takes many seconds before prey is immobilized.

The experiments described herein explored the mechanistic basis for the very rapid immobilization of fish prey by a different cone snail, *Conus purpurascens*, the purple cone. Remarkably, it was found that two entirely distinct physiological programs are elicited by the venom: not only does this snail block neuromuscular transmission using multiple neurotoxins, but the data demonstrate that the snail also uses excitotoxins which act synergistically to "shock" prey into an immobilized, rigid state. A novel $K^+$ channel-targeted conotoxin participates in the latter program. It is suggested that the two parallel physiological programs elicited by *Conus purpurascens* venom represent general strategies widely used for prey capture by other venomous animals, and that much of the confusing toxin diversity described in venoms can be understood by considering these physiological frameworks.

Biology of *Conus purpurascens*: the net vs. hook-and-line strategy. *Conus geographus*, the first cone snail analyzed in detail (Olivera et al., 1985), uses a "net" strategy for capturing prey; when it detects fish, it opens its mouth (rostrum) very wide and the unwary fish that gets too close is engulfed by the distended mouth, and then stung. In contrast, the purple cone, *Conus purpurascens*, is a fish-hunting species which basically uses a hook-and-line strategy. The snail injects approximately 5 μl of venom into its fish prey through a harpoon-like tooth which serves not only as a disposable hypodermic needle but also to tether prey. The fish is almost instantaneously immobilized by a good strike. Numerous aquarium observations have revealed that this initial stage of immobilization is always characterized by a rigid tetanic extension of the major fins. This initial symptomatology is referred to as the Sudden Tetanus Of Prey (or STOP) syndrome. Occasionally, a fish recovers from this tetanic state, begins moving again, but later becomes paralyzed in a flaccid state. Generally, the fish is engulfed by the mouth of the snail during the initial phase of tetanic paralysis.

As was previously described elsewhere, *Conus purpurascens* venom contains as one of its major components a peptide which is targeted to the nicotinic acetylcholine receptor. This venom component, αA-conotoxin PIVA (Hopkins et al., 1995) blocks synaptic transmission and causes paralysis and death of fish. More recently, at least two other venom peptides which cause flaccid paralysis and death have been characterized from *Conus purpurascens* venom; one of these, μ-conotoxin PIIIA inhibits action potential propagation in skeletal muscle by blocking voltage-gated sodium channels (Shon et al., 1996). Injection of any of these toxins into fish elicits a generalized flaccid paralysis, an effect entirely distinct from the STOP syndrome. Thus, it appears that like *Conus geographus*, *C. purpurascens* produces multiple toxins which act synergistically to block neuromuscular transmission. However, there must be other components of *C. purpurascens* venom responsible for the STOP syndrome.

SUMMARY OF THE INVENTION

The present invention is directed to a conotoxin peptide having 27 amino acids, six cysteines which form three disulfide bonds between the first and fourth, second and fifth, and third and sixth cysteines, respectively. The invention is directed to κ-conotoxin PVIIA having the formula Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO:1) where Xaa represents 4-transhydroxyproline hydroxproline or proline. This peptide targets voltage-gated potassium channels.

BRIEF DESCRIPTION OF THE FIGURES

FIG. 1A. *Conus purpurascens* specimens were milked as previously described (Hopkins et al., 1995). The milked venom was pooled, and fractionated by high performance liquid chromatography; the elution profile is shown in FIG. 1A (Shon et al., 1995). The peaks indicated by the bar contain the lock-jaw peptide (δ-conotoxin PVIA); the purification and biochemical characterization of this peptide has recently been described (Shon et al., 1996). The peak indicated by the arrow is the fin-popping peptide (κ-conotoxin PVIIA) described in the text.

DETAILED DESCRIPTION OF THE PREFERRED EMBODIMENT

The present invention is directed to a conotoxin peptide having 27 amino acids, six cysteines which form three disulfide bonds between the first and fourth, second and fifth, and third and sixth cysteines, respectively, and to the precursors of these peptides. The invention is directed to κ-conotoxin PVIIA having the formula Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO: 1) where Xaa represents 4-trans-hydroxyproline. This peptide targets potassium channels and may be used to augment neurotransmitter release in a number of pathological situations, for example in Alzheimer's disease. Potassium channel inhibitors such as κ-conotoxin PVIIA augment release of neurotransmitters at synapses in autoimmune diseases such as the Lambert-Eaton syndrome or myasthenia gravis and have a utility for alleviating these medical conditions.

Chemical Synthesis of Conotoxins

These peptides are sufficiently small to be chemically synthesized. General chemical syntheses for preparing the foregoing conotoxin peptides are described hereinafter, along with specific chemical syntheses of several conotoxin peptides and indications of biological activities of these synthetic products. Various ones of these conotoxin peptides can also be obtained by isolation and purification from specific Conus species using the technique described in U.S. Pat. No. 4,447,356 (Olivera et al., 1984), the disclosure of which is incorporated herein by reference.

Although the conotoxin peptides of the present invention can be obtained by purification from cone snails, because the amounts of conotoxin peptides obtainable from individual snails are very small, the desired substantially pure conotoxin peptides are best practically obtained in commercially valuable amounts by chemical synthesis. For example, the yield from a single cone snail may be about 10 micrograms or less of conotoxin peptide. By "substantially pure" is meant that the peptide is present in the substantial absence of other biological molecules of the same type; it is preferably present in an amount of at least about 85% by weight and preferably at least about 95% of such biological molecules of the same type which are present (i.e., water, buffers and innocuous small molecules may be present). Chemical synthesis of biologically active conotoxin peptides depends of course upon correct determination of the amino acid sequence.

The conotoxin peptides can also be produced by recombinant DNA techniques well known in the art. Such techniques are described by Sambrook et al. (1979). The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conotoxin molecule. However, because of the dilution resulting from the presence of other fractions of less biopotency, a somewhat higher dosage may be required.

A second method of forming the disulfide bonds in the conotoxin peptides of the present invention involves the use of acetamidomethyl (Acm) as protection agent on the second and fifth cysteines during the synthesis of the conotoxin peptides. The use of Acm on these two residues is based on the analogy with disulfide bridges in other conotoxin peptides. The peptide with the Acm protected cysteines is air-oxidized overnight at room temperature. The bicyclic peptides are separated by high performance liquid chromatography (HPLC) and the desired isomer isolated. The final disulfide bridge is carried out by iodination. The undesired isomers are efficiently recycled by reduction to linear peptide. The desired isomer is determined by a partial reduction analysis (Gray, 1993). In this analysis, a sample of a bicyclic precursor is treated with tris-[2-carboxyethyl]-phosphine to give linear peptide and a singly-bridged intermediate. The latter peptide is reacted with iodoacetamide, and the location of alkylated cysteine residues is established by sequence analysis. In this analysis, it was determined that the correct linkages were between the first and fourth, second and fifth, and third and sixth cysteines.

The peptides are synthesized by a suitable method, such as by exclusively solid-phase techniques, by partial solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventional solution phase peptide synthesis, the peptide chain can be prepared by a series of coupling reactions in which the constituent amino acids are added to the growing peptide chain in the desired sequence. The use of various N-protecting groups, e.g., dicyclohexylcarbodi-imide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. Nos. 3,842,067 (1974) and 3,862,925 (1975).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chin protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al., (1966). Chloromethylated resins are commercially available from Bio Rad Laboratories (Richmond, Calif.) and from Lab. Systems, Inc. The preparation of such a resin is described by Stewart et al. (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH—MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carded out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):CH$_2$Cl$_2$ (1:1) or in DMF or CH$_2$Cl$_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF), followed by oxidation as described above.

EXAMPLE I

Identification of venom constituents involved in STOP. The venom of *Conus purpurascens* was separated into its major components by high performance liquid chromatography (see FIG. 1A). Each major component of the venom was individually bioassayed by injection into goldfish; several caused flaccid paralysis and death, but none of the individual fractions elicited a physiological effect which closely resembled the STOP syndrome.

Pairs of venom components in combination were tested to determine if the pairs would elicit the STOP syndrome. When injected together, two chromatographic fractions (corresponding to the fractions shown with the arrow and the bar in FIG. 1A) resulted in STOP symptomatology. The first component (peak with arrow) is an activity which is here called "the fin popping peptide"; the purification and characterization of this component is described below. The fraction indicated by the bar is a venom component recently purified and chemically synthesized, which is referred to as the "lock-jaw peptide," also called δ-conotoxin PVIA (Shon et al., 1995).

Although the two peptides together elicit the STOP syndrome, injection of the fin-popping peptide by itself yielded symptomatology that diverged significantly from STOP. The fish became noticeably hyperactive, moving continuously and in a jittery manner against the glass wall of the aquarium. After some time, the fish would characteristically contract then suddenly extend all major fins (producing a "fin-pop"). This fin-popping behavior would be repeated more or less continuously, causing a series of rather jerky movements. Even when injected in large doses, the purified fin-popping peptide did not cause either immobilization or death. In contrast, envenomated fish exhibiting the full-blown STOP syndrome perform a single, irreversible, and ultimately lethal "fin-pop."

The second component required to elicit STOP is the lock-jaw peptide, δ-conotoxin PVIA (δ-PVIA). When injected into prey, the purified peptide caused an initial quiescent period followed by a transition often characterized by jaw extension (the lock-jaw symptom), which was in turn followed by the fish swimming in long, extremely jerky runs; the jerks were violent enough to often cause the fish to bump into the sides of the aquarium. After this period of violent swimming, the fish would exhibit a generalized rigid paralysis from which they would not generally recover. In this respect, the action of the lock-jaw peptide had some elements in common with the STOP syndrome, except that with the latter, the long quiescent period and brief transitional period of violent swimming were not observed.

To elicit typical STOP symptomatology a combination of both peptides is required. It is likely that additional components of the venom contribute to STOP in vivo; given a good strike by the snail, fin tetanus is elicited in one or two seconds. Although the two purified components injected together elicit STOP, the time-of-onset is significantly longer.

EXAMPLE 2

Purification and biochemical characterization of the "fin-popping peptide." In order to investigate the venom component responsible for the fin-popping activity, it was purified to homogeneity from *Conus purpurascens* venom (shown in FIGS. 1A–1C). The amino acid sequence determined by standard Edman sequencing methods revealed a 27-amino acid peptide (Table I). Chemical synthesis of biologically active peptide and molecular cloning have been accomplished. The amino acid sequencing, chemical synthesis, cloning and mass spectrometry all confirm that the fin-popping activity stems from a novel peptide with three disulfide bonds; its sequence is:

CRIXNQKCFQHLDDCCSRKCNRFNKCV (SEQ ID NO:1)

(where X=4-trans-hydroxyproline)

This peptide has the same arrangement of Cys residues observed in other families of conotoxins, notably the ω-conotoxins which block voltage-gated calcium channels, and the δ-conotoxins which inhibit the inactivation of voltage-gated sodium channels (Shon et al., 1995). It was directly tested whether the peptide competes with either radiolabeled ω-conotoxins or δ-conotoxin; no displacement of specific binding was seen, even at micromolar concentrations of the fin-popping peptide (results not shown). Thus, the fin-popping peptide appears to target a receptor site different from the $Ca^{+2}$ and $Na^{+}$ channel target sites of the ω-and δ-conotoxins.

TABLE I

Sequence Analysis of the Fin-Popping Peptide

| Step | Amino Acid | Yield (pmol) |
|------|------------|--------------|
| 1 | Cys | 29.6 |
| 2 | Arg | 87.4 |
| 3 | Ile | 89.8 |
| 4 | Hyp | 29.7 |
| 5 | Asn | 70.4 |
| 6 | Gln | 58.6 |
| 7 | Lys | 28.5 |
| 8 | Cys | 57.4 |
| 9 | Phe | 64.1 |
| 10 | Gln | 49.7 |
| 11 | His | 28.4 |
| 12 | Leu | 54.4 |
| 13 | Asp | 45.4 |
| 14 | Asp | 56.0 |
| 15 | Cys | 40.3 |
| 16 | Cys | 45.9 |
| 17 | Ser | 10.8 |
| 18 | Arg | 33.1 |
| 19 | Lys | 8.2 |
| 20 | Cys | 19.9 |
| 21 | Asn | 20.8 |
| 22 | Arg | 21.8 |
| 23 | Phe | 21.1 |
| 24 | Asn | 21.5 |
| 25 | Lys | 7.7 |
| 26 | Cys | 9.1 |
| 27 | Val | 2.5 |

Predicted sequence:

Cys.Arg.Ile.Hyp.Asn.Gln.Ly-
s.Cys.Phe.Gln.His.Leu.Asp.Asp.Cys.Cys.Ser.Arg.Lys.Cys.Asn.
Arg.Phe.Asn.Lys.Cys.Val. (SEQ ID NO:1)

Legend to Table I.

The fin-popping peptide was purified as shown in FIGS. 1A–1D, and the sequence determined using methods previously described (Shon et al., 1995).

EXAMPLE 3

Figure 1A:
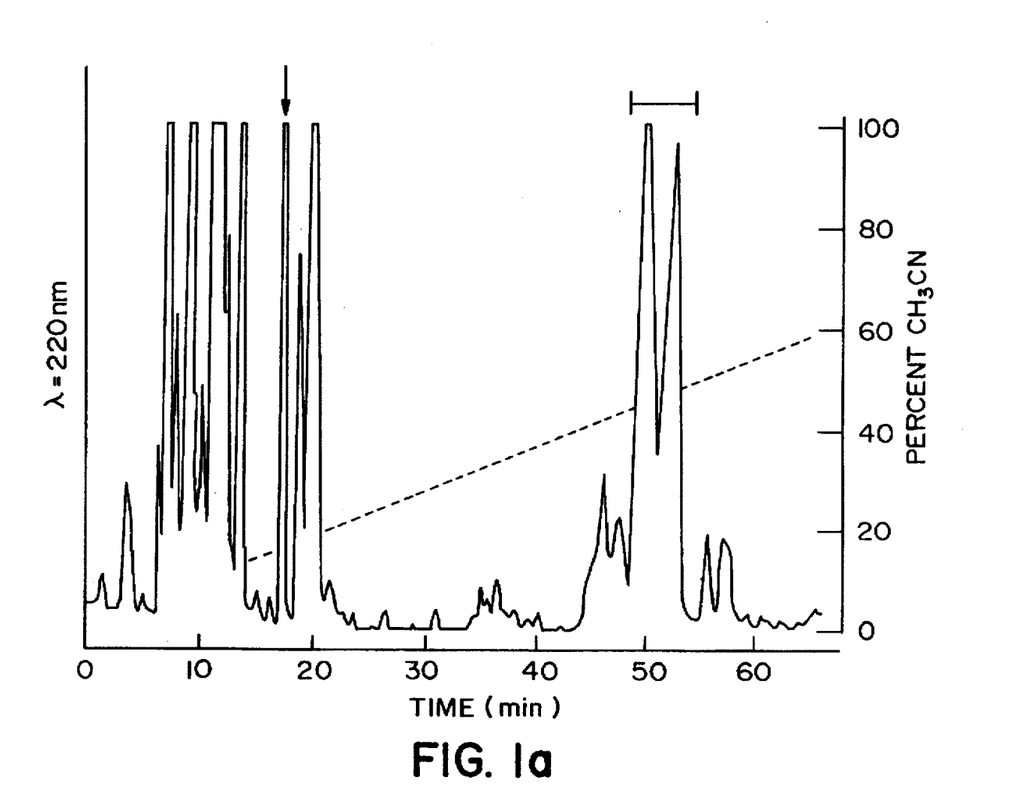
Figure 1B:
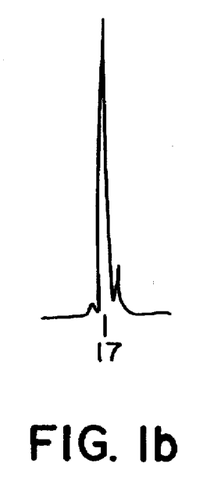
FIGS. 1B and 1C. The peak from FIG. 1A was rechromatographed twice by HPLC with the standard TFA/acetonitrile buffer system; the gradient was 12–30% acetonitrile, 0.1% TFA. The fin-popping peptide elutes at 22% acetonitrile.
Figure 1C:
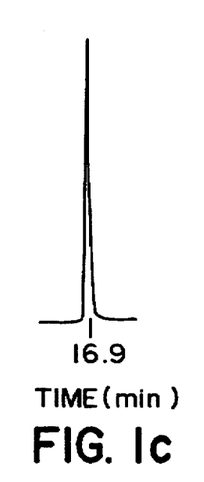
Figure 1D:
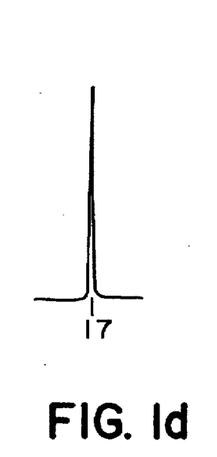
FIG. 1D. An equal amount of native and synthetic peptide were mixed and co-eluted at 22% acetonitrile as a single homogeneous peak, indicating that the sequence assignment could be verified by synthesis.
Figure 2A:
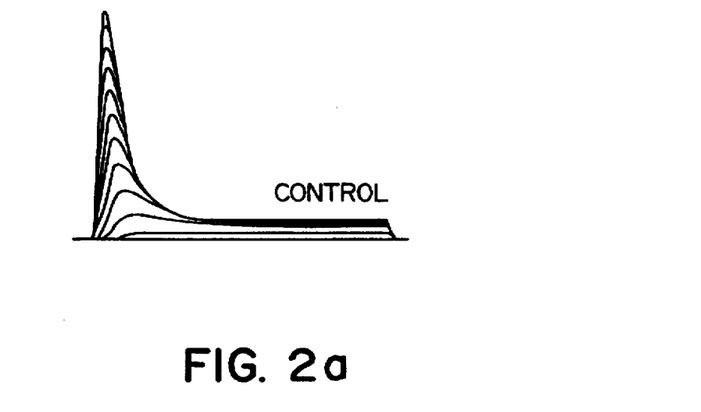
FIG. 2A. κ-Conotoxin PVIIA blocks the Shaker K⁺ channel. Whole cell currents from an oocyte expressing Shaker H4 K⁺ channels (Kamb et al., 1988) evoked by test potentials of -80 to +60 mV in steps of 10 mV.
Figure 2B:
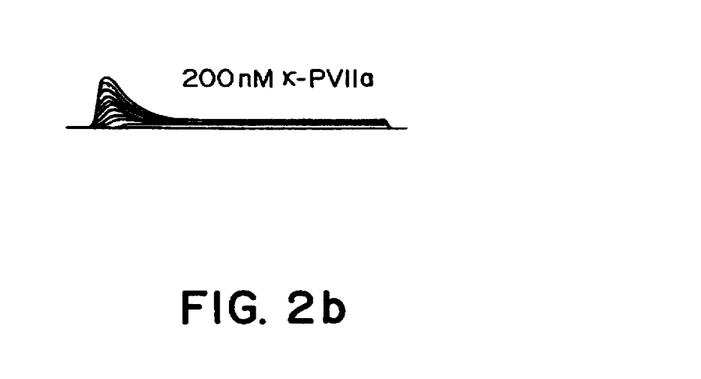
FIG. 2B. Presence of 200 nM κ-conotoxin PVIIA in the bath solution reduces the peak current amplitude to about 20% of the control value.
Figure 2C:
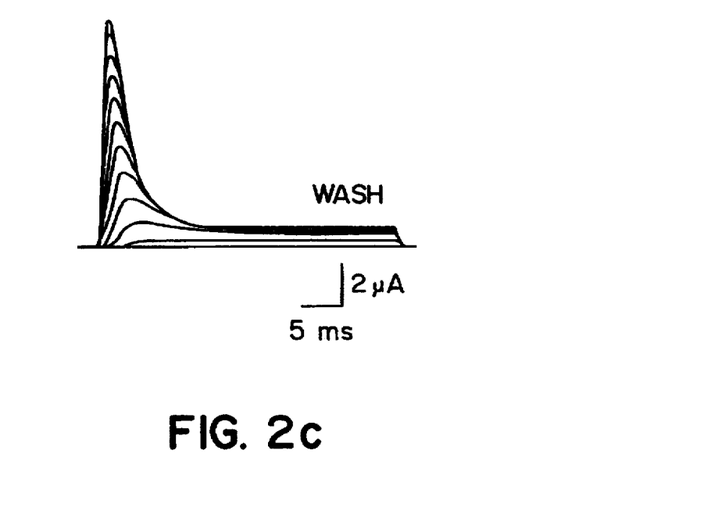
FIG. 2C. The reduction seen in FIG. 2B is reversible as seen here following a wash step to remove the added κ-conotoxin PVIIA.
Figure 2D:
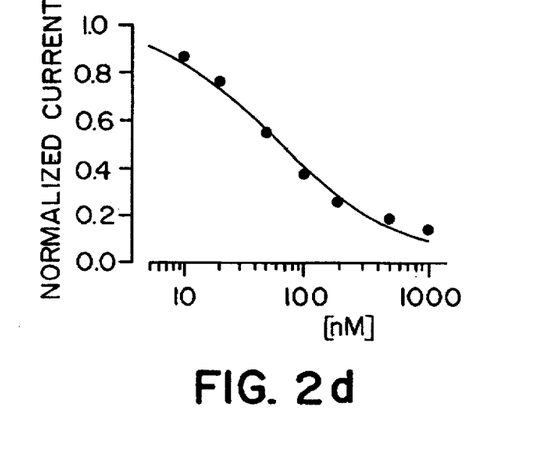
FIG. 2D. Dose-response curve for the block by κ-conotoxin PVIIA at a test potential of +40 mV.

Electrophysiological characterization. The binding competition experiments above suggested that the fin-popping peptide, though structurally related, is neither an ω-nor a δ-conotoxin. Experimental evidence for the underlying physiological mechanism of action of the fin-popping peptide is shown in FIGS. 2A–2F. The pure toxin was tested on an oocyte expressing the Shaker $K^+$ channel cloned from *Drosophila melanogaster*. Capped run-off Shaker cRNA for injection into Xenopus oocytes was synthesized using a template with a T7 promotor by a standard protocol (Krieg and Melton, 1987). Oocyte injection was performed as described (Stühmer, 1992). Kv1.1 (Baumann et al., 1988) and Kv.14 (Stühmer et al., 1989) were reclone by PCR. Whole cell currents were measured with a two-electrode voltage clamp (Stühmer, 1992). Current records were low-pass filtered at 1 kHz (−3 dB) and sampled at 4 kHz. The bath solution was normal frog Ringer's (NFR) containing (in mM): 115 NaCl, 2.5 KCl, 1.8 $CaCl_2$, 10 HEPES pH 7.2 (NaOH). To estimate the $IC_{50}$ of κ-conotoxin PVIIA, whole cell currents of oocytes expressing Shaker H4 $K^+$ channels were measured while the toxin concentration in the bath was successively increased. The peak current at a given voltage was measured and plotted against the toxin concentration. Dose-response curves were fitted to the equation $y=(1+(T/IC_{50})^n)^{-1}$ where "T" is the toxin concentration and "n" the Hill coefficient. The Hill coefficient was about 1. All electrophysiological experiments were performed at room temperature (19°–22° C.). As shown in FIG. 2B, the toxin at a concentration of 200 nM blocked the $K^+$ conductance of the expressed Shaker channel, indicating that the peptide targets voltage-gated potassium channels. A dose response is shown in FIG. 2D.

Figure 2E:
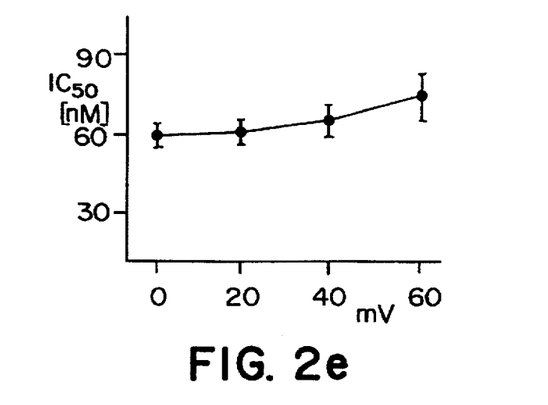
FIG. 2E. IC$_{50}$ of the block by κ-conotoxin PVIIA at different test potentials (mean±S.E.M., n=5).
Figure 2F:
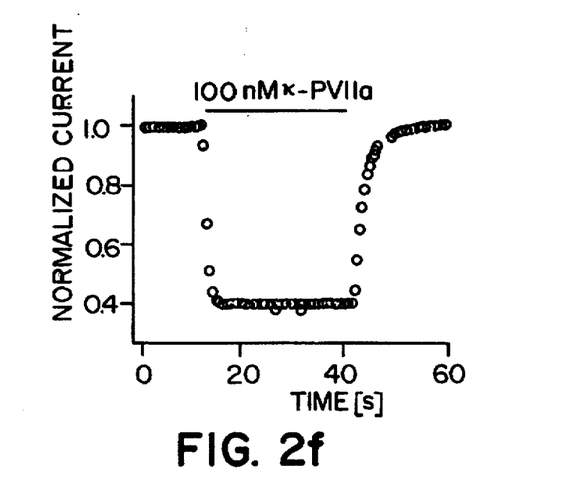
FIG. 2F. Example of the kinetics of the block by 100 nM κ-conotoxin PVIIA. Steady-state of block was reached in less than 5 seconds and the wash out was complete in less than 15 seconds (n=8). Identical kinetic results were obtained with 20 nM (n=5) and 1000 nM (n=6) κ-conotoxin PVIIA indicating a very fast block of the toxin.
Figure 3A:
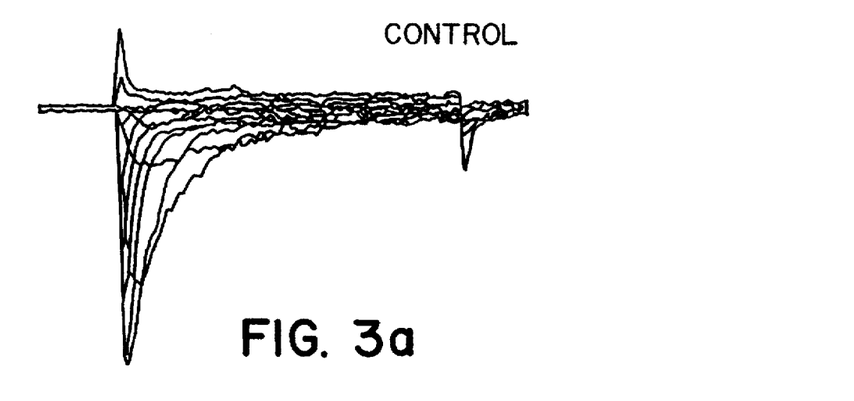
FIG. 3A. δ-Conotoxin PVIA slows the fast inactivation of Na⁺ currents. Na⁺ currents recorded from a nucleated patch from a hippocampal cell in culture. Currents were evoked by test potentials of -60 to +60 mV in steps of 10 mV from a holding potential of -80 mV. This figure represents data from a control experiment.
Figure 3B:
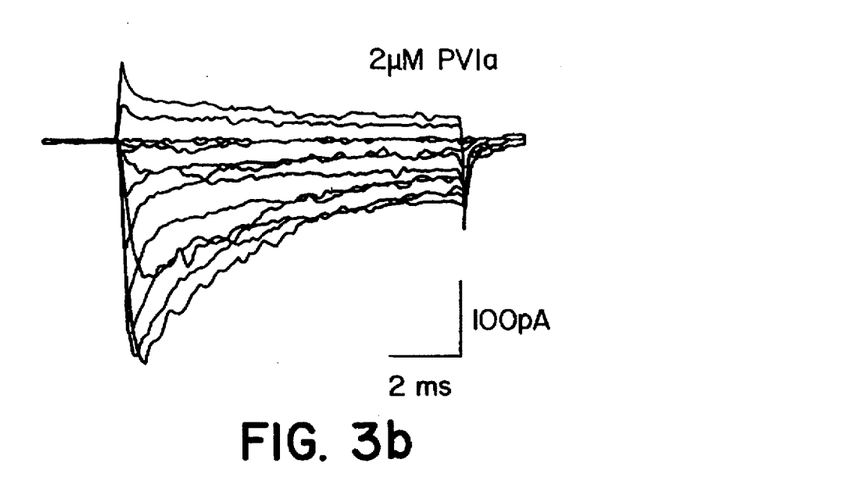
FIG. 3B. Data from an experiment as shown in FIG. 3A but in the presence of 2 μM PVIA.
Figure 3C:
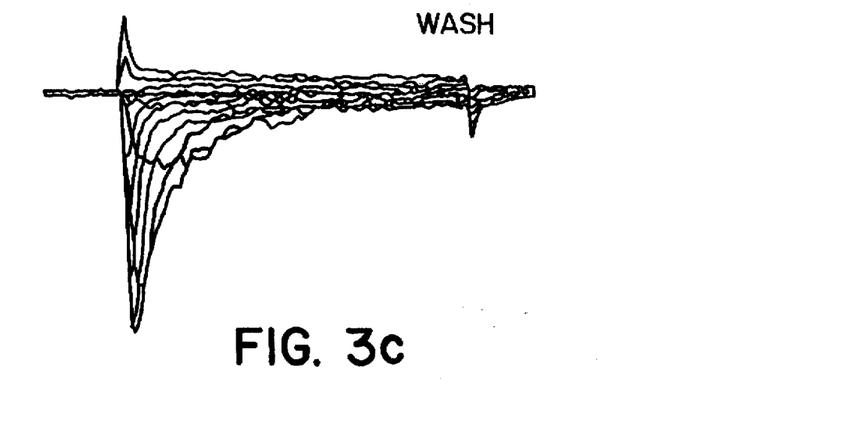
FIG. 3C. Data shown for the same experiment as in FIG. 3B following a wash to remove the PVIA.
Figure 3D:
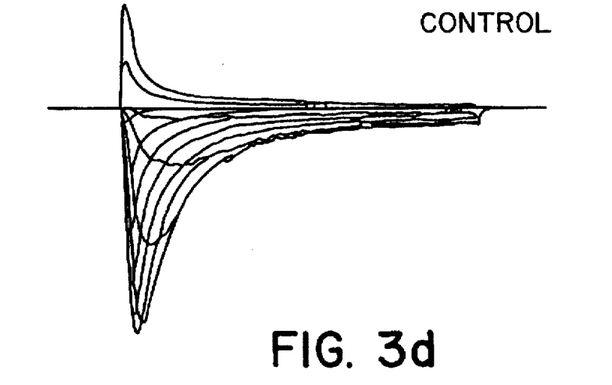
FIG. 3D. Na⁺ currents from an outside-out macropatch excised from a Xenopus oocyte expressing rat brain Na⁺ channel II. Patches were depolarized from a holding potential of -100 mV to test potentials ranging from -80 to +60 mV in steps of 10 mV. The results of a control experiment are shown.
Figure 3E:
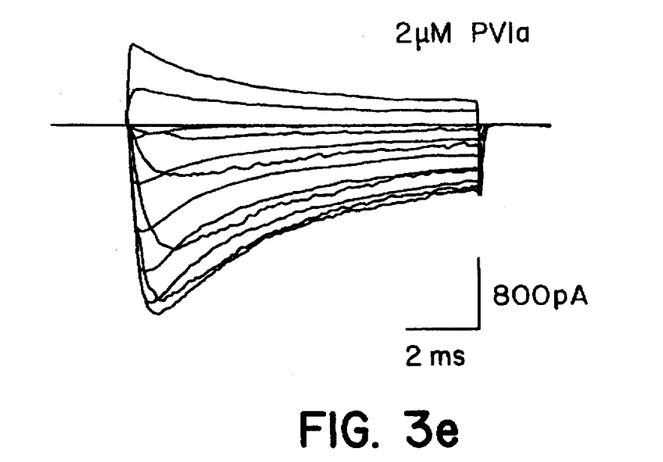
FIG. 3E. The same experiment as in FIG. 3D but in the presence of 2 μM PVIA.
Figure 3F:
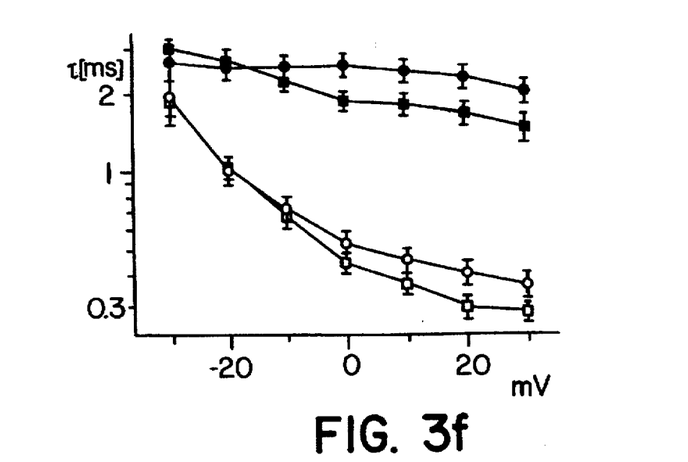
FIG. 3F. Time constants of inactivation of the Na⁺ currents plotted as a function of the test potential for nucleated patches from hippocampal neurons (squares, n=11) and outside-out macropatch excised from an oocyte expressing rat brain Na⁺ channel II (circles, n=10). Open symbols represent the values under control conditions and closed symbols after addition of 2 μM PVIA. Values are given as mean±S.E.M. Values are from non-linear least-square fits according to the description of sodium current kinetics by Hodgkin and Huxley (1952) assuming one inactivation gate.

The $IC_{50}$ of the peptide for Shaker-mediated currents was determined at different test voltages (FIG. 2E). Under the experimental conditions used, the $IC_{50}$s ranged from 60±3 nM (at 0 mV) to 70±6 nM (at +60 mV), indicating only a slight voltage dependence of the blocking effect of the toxin (FIG. 2E). Not surprisingly, given the very rapid physiological response in vivo, kinetics of block appear to be very fast. For the concentrations tested (20 nM, 100 nM and 1000 nM), steady state block was reached in a few seconds as shown in FIG. 3F. Although the peptide has effects in vertebrate systems, as evidenced by the excitatory symptomatology elicited in both fish and mice in vivo, no cloned vertebrate $K^+$ channel subtype has yet been identified which is potently inhibited by the peptide; at 1 μM, the peptide has no effect on $K^+$ channels Kv1.1 or Kv1.4 from rat brain (not shown). These results establish that the fin-popping peptide does not belong to previously characterized conotoxin families but is instead the first member of a putative conotoxin family of $K^+$ channel-targeted peptides. This family is here designated the κ-conotoxins, and the fin-popping peptide from *Conus purpurascens* as κ-conotoxin PVIIA (κ-PVIIA).

EXAMPLE 4

The lock-jaw peptide: activity in neuronal systems. The other venom component required for STOP is the lock-jaw peptide, δ-conotoxin PVIA (δ-PVIA) (Shon et al., 1995). Previously, this 29-amino acid peptide was shown to increase excitability in frog neuromuscular preparations. On the basis of this activity and its homology to δ-conotoxins from snail-hunting Conus, it was hypothesized that the peptide increased $Na^+$ conductance through voltage-gated $Na^+$ channels. The experiments in FIGS. 3A–3F clearly demonstrate that the peptide delays $Na^+$ channel inactivation in vertebrate CNS neurons.

The effects of δ-PVIA on rat brain type II sodium channels expressed in oocytes, as well on $Na^+$ currents recorded from hippocampal cells are shown in FIGS. 3A–3F.
Methods.

Rat hippocampal cultures were obtained as in Seifert et al. (1983). Recordings were taken after 4–7 days in culture. Since the processes of the neurons precluded a good voltage control during clamp experiments in the whole-cell configuration (Hamill et al., 1981 ), nucleated patch recordings (Sather et al., 1992) were performed. The pipettes had resistances of 2–3 MΩ and contained (in mM) 100 CsCl, 10 NaCl, 20 phosphocreatine, 50 units of creatine phosphokinase per ml, 4 MgATP, 10 EGTA and 10 HEPES-CsOH (pH 7.2). The bath solution contained (in mM) 140 NaCl, 2.8 KCl, 2 $CaCl_2$, 2 $MgCl_2$ and 10 HEPES-NaOH (pH 7.2). Currents were measured with an EPC-9 patch clamp amplifier driven by the Pulse+PulseFit software package (HEKA Elektronik, Lainbrecht, Germany). Current records were low-pass filtered at 3 kHz (−3dB) and sampled at a rate of 10 kHz. Leak and capacitive currents were corrected on-line with a P/n method.

Rat brain $Na^+$ channel II cRNA (Noda et al., 1986) for injection into Xenopus oocytes was synthesized using a template with an SP6 promotor. Currents were recorded 2–5 days after injection. The recording pipettes with resistances of 0.8–1.4 MΩ were either filled with 100 mM KCl, 16 mM NaCl, 1.8 mM EGTA and 10.0 mM HEPES-KOH (pH 7.2) for outside-out patches or with NFR for inside-out patches.

Current records were low-pass filtered at 5 kHz (−3 dB) and sampled at 20 kHz. The bath solution contained NFR for outside-out recordings and 100 mM KCl, 16 mM NaCl, 1.8 mM EGTA, 10.0 mM HEPES-KOH (pH 7.2) for inside-out recordings. Since PVIA is very hydrophobic, a concentrated stock solution of the toxin was added to the bath chamber (0.8–1.2 ml) with a Gilson pipetter. The indicated toxin concentration corresponds to the final concentration in the bath chamber.

The normally rapid inactivation of voltage-gated sodium conductance is suppressed, and the duration of the macroscopic $Na^+$ current is prolonged (FIGS. 3A–3E). The effect of δ-PVIA on the $Na^+$ currents is reversible (as shown for neurons in FIGS. 3A–3C). δ-PVIA had no effect when applied to the cytoplasmic side of inside-out patches excised from an oocyte expressing rat brain Type II $Na^+$ channels indicating that the toxin targets an extracellular site on the channel complex. The peptide had no effect on any $K^+$ channel subtype tested (Kv1.1, Kv1.4 and Shaker H4).

Two physiological programs: excitotoxic shock vs. neuromuscular block. The electrophysiological results above indicate that when Conus purpurascens stings a fish, the STOP syndrome is elicited in prey by two peptides acting synergistically. Both are in effect, excitotoxins: one increases $Na^+$ influx while the second decreases $K^+$ efflux.

Thus, the purple cone appears to use two entirely distinct programs for immobilizing (and ultimately killing) fish. The toxins which inhibit acetylcholine receptors and voltage-gated $Na^+$ channels are part of the general venom strategy to block neuromuscular transmission, resulting in flaccid paralysis. The fin-popping peptide (κ-PVIIA) and lock-jaw peptide (δ-PVIA) are key components for an alternative excitotoxic shock program elicited by the venom; this quickly results in a rigid (as opposed to flaccid) paralysis of the prey. Since Conus purpurascens has clearly evolved highly potent neurotoxins which inhibit neuromuscular transmission, why would the snail need to have excitotoxins in addition? In order to address this question, some potentially limiting features of a strategy of inhibiting neuromuscular transmission need to be addressed.

Conotoxins that are components of a concerted program to cause neuromuscular block appear to be optimized in several ways. Their small size and compact shape facilitates rapid dispersal through the body of the prey. (Olivera et al., 1990) The presence of venom components, such as the conopressins (Cruz et al., 1987) indicates that there may be additional venom peptides which accelerate delivery of neurotoxins to neuromuscular junctions. Nevertheless, significant theoretical drawbacks still remain with regard to a neuromuscular block program, if speed of immobilization limits success of prey capture.

In order to immobilize fish, it would clearly be necessary to get the neurotoxins from the injection site to the major fin musculature. In addition to the delay that this necessarily entails, the "safety margin" of certain physiological components involved in transmission could be an additional limiting factor. If blocking neuromuscular transmission required that over 90% of a particular component be functionally inhihibited, the concentration of the blocking toxin at the site must be more than ten-fold the dissociation constant of the toxin. Thus, in order to immobilize prey by muscular paralysis, the relevant neurotoxins not only have to be conveyed to the appropriate neuromuscular junction, but have to be highly effective in functionally inhibiting the targeted physiological components there.

In contrast, an excitotoxic strategy might not have to affect even a majority of the molecular components targeted (the voltage-gated sodium channels and potassium channels, for example). It may be necessary in a particular circuit to activate just enough sodium channels and inhibit just enough potassium channels to tilt the balance so that the target circuit fires, requiring far fewer toxin molecules. In addition, excitotoxins may act at (or very close to) the site of venom injection instead of at distant neuromuscular junctions throughout the body of the prey. A powerful local depolarization may be sufficient to functionally immobilize a whole organism extremely rapidly (rather like a power surge wiping out a computer). The systems level circuitry and precise physiological responses that initiate rapid knock-out of fish remain to be elucidated.

Thus, if speed of prey immobilization is the dominant consideration, an excitotoxic shock program could have at least two advantages. From the point of venom injection, excitotoxic effects can be propagated at the speed of action potentials; in contrast, neuromuscular blocking peptides would be dispersed much more slowly. Furthermore, excitotoxic shock would not be deterred by the blood/brain barrier; CNS control circuits (such as the escape response center) can be disrupted rapidly; in contrast, neurotransmission blockers have to be "decentralized" at multiple neuromuscular junctions in the periphery.

Other venomous predators, evolutionary considerations. The STOP syndrome is a specific manifestation in fish of the more general physiological strategy which is here called excitotoxic shock. It is suggested that for many venomous predators, neuromuscular block and excitotoxic shock are two alternative general physiological programs; Conus purpurascens is unusual in having a venom which elicits both.

Some venomous predators appear to be clearly tilted towards using neuromuscular block. Thus, elapid snakes have as a dominant component in their venom α-neurotoxins which block the nicotinic acetylcholine receptor (Chang, 1979). Spiders have both blockers of presynaptic calcium channels as well as postsynaptic glutamate receptors (Adams and Swanson, 1994). In Conus geographus venom, all major paralytic toxins contribute to neuromuscular block (Olivera et al., 1985). Thus, for all of these cases, excitotoxic shock appears either to be absent or to play a very minor role—neuromuscular block is the dominant physiological strategy.

In contrast, other venomous predators appear to use excitotoxic shock as a major physiological program. For example, scorpions have potent neurotoxins which greatly increase $Na^+$ conductance (Strichartz et al., 1987) and decrease $K^+$ conductance (Carbone et al., 1982; Possani et al., 1982). Certain snail-hunting cone snails, such as Conus gloriamaris (Shon et al., 1994) have a δ-conotoxin which would increase $Na^+$ conductance as a major component of their venom. Sea anemones have both peptides which increase sodium conductance and voltage-gated potassium channel inhibitors as well (Beress et al., 1977; Rathmayer, 1979; Lazdunski et al., 1987; Karlsson et al., 1991; Aneiros et al., 1993; Castañeda et al., 1995; Schweitz et al., 1995). In these three cases the venom appears to be strongly (and perhaps exclusively) focused on excitotoxic shock.

The ability to immediately immobilize prey is probably increasingly critical the less mechanically well-secured the prey is at the time of initial capture. Venomous predators using neuromuscular block either are able to "chase" their increasingly paralyzed prey or appear to have generally well-secured prey. Conus geographus (which employs a net strategy to capture its prey) has essentially engulfed a fish completely before it stings; a sea snake which preys on much smaller fish will have firmly gripped the prey with its fangs at the time venom is injected. Ingesting flaccid prey is no doubt preferable to swallowing a stiff and rigid one.

In contrast, if the initial mechanical seizure of prey is much more precarious (such as in hook-and-line-hunting cone snails like *Conus purpurascens*, or in sea anemones) or even non-existent (such as for electric fish), then a massive depolarization induced at one site may be a necessary strategy, particularly if the predator cannot pursue the prey effectively (i.e., a relatively immobile predator and/or prey which can move in a different dimension). Animals such as sea anemones which have a tenuous hold on much more mobile prey have evolved primary neurotoxins in their venoms which increase $Na^+$ conductance and block $K^+$ conductance, and may have dispensed with neuromuscular block altogether.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Adams, M. E. & Swanson, G. *TINS* S1–S29 (1994).
Aneiros, A. et al. (1993). *Biochim. biophys. Acta* 1157:86–92.
Baumann, A., Grupe, A., Ackermann, A. & Pongs, O. (1988). *EMBO J.* 7:2457–2463.
Beress, L., Wunderer, & Wachter (1977). E. *Hoppe*-Seyler's Z. Physiol. Chem. 358:985–988.
Bodansky et al. (1966). *Chem. Ind.* 38:1597–98.
Carbone, E. et al. (1982). *Nature* 296:90–91.
Castañeda, O. et al. (1995). *Toxicon* 33:603–613.
Chang, C. C. in *Snake Venoms. Handbook of Experimental Pharmacology* v. 52 (ed. Lee, C.-Y.) (Springer-Verlag, Berlin, 1979).
Cruz, L. J. et al. (1987). *J. Biol. Chem.* 262:15821–15824.
Gray, W. R. (1993). Disulfide Structures of Highly Bridged Peptides: A New Strategy for Analysis. *Protein Science* 2:1732–1748.
Hamill, O. P., Marty, A., Neher, E., Sakmann, B. & Sigworth, F. J. (1981). *Pflügers Arch. Eur. J. Physiol.* 391:85–100.
Hodgkin, A. L. & Huxley, A. F. (1952). *J. Physiol.* 117:500–544.
Hopkins, C. et al. (1995). *J. Biol. Chem.* 270:22361–22367.
Horiki, K. et al. (1978). *Chemistry Letters* 165–68.
Kaiser et al. (1970). *Anal. Biochem.* 34:595.
Kamb, A., Tseng-Crank & Tanouye, M. A. (1988). *Neuron* 1:421–430.
Kapoor (1970). *J. Pharm. Sci.* 59:1–27.
Karlsson, E. et al. (1991). *Toxicon* 29:1168.
Kornreich, W. D. et al. (1986). U.S. Pat. No. 4,569,967.
Krieg, P. A. & Melton, D. A. (1987). *Meth. Enzymol.* 155:397–415.
Lazdunski, M. et al. (1987). *Ann. N.Y. Acad Sci.* 479:204–220.
*Methoden der Organischen Chemie* (Houben-Weyl). *Synthese von Peptiden*, E. Wunsch (Ed.), Georg Thieme Verlag, Stuttgart, Ger. (1974).
Myers, R. A., Cruz, L. J., Rivier, J. & Olivera, B. M. (1993). *Chem. Rev.* 93:1923–1936.
Noda, M. et al. (1986). *Nature* 320:188–191.
Olivera, B. M. et al. (1984). U.S. Pat. No. 4,447,356.
Olivera, B. M. et al. (1985). *Science* 230:1338–1343.
Olivera, B. M. et al. (1990). *Science* 249:257–263.
Possani, L. D., Martin, B. M., & Svendensen, I. (1982). *Carlsberg Res. Commun.* 47:285–289.
Rathmayer, W. (1979). *Adv. Cytopharmacol.* 3:335–344.
Rivier, J. R. et al. (1978). *Biopolymers* 17:1927–38.
Sambrook, J. et al. (1979). *Molecular Cloning: A Laboratory Manual*, 2nd Ed., Cold Spring Harbor Laboratory, Cold Spring Harbor, N.Y.
Sather, W., Dieudonne, S., MacDonald, J. & Ascher, P. (1992). *J. Physiol.* 450:643–672.
Schroder & Lubke (1965). *The Peptides* 1:72–75, Academic Press, N.Y.
Schweitz, H. et al. (1995). *J. Biol. Chem.* 270:25121–25126.
Seifert, W., et al. in *Neurobiology of the Hippocampus* (ed. Seifert, W.) 109–135 (Academic, London, 1983).
Shon, K. et al. (1994). *Biochemistry* 33:11420–11425.
Shon, K. et al. (1995). *Biochemistry* 34:4913–4918.
Shon, K. et al. (1996). *J. Biol. Chem.* submitted.
Stewart and Young, *Solid-Phase Peptide Synthesis*, Freeman & Co., San Francisco, Calif. (1969).
Strichartz, G., Rando, T. & Wang, G. K. (1987). *Ann. Rev. Neurosci.* 10:237–267.
Stühmer, W. (1992). *Meth. Enzymol.* 207:319–339.
Stühmer, W. et al. (1989). *EMBO J.* 8:3235–3244.
Vale et al. (1978). U.S. Pat. No. 4,105,603.
U.S. Pat. No. 3,972,859 (1976).
U.S. Pat. No. 3,842,067 (1974).
U.S. Pat. No. 3,862,925 (1975).

---

What is claimed is:

1. A substantially pure κ-conotoxin peptide consisting of the amino acid sequence Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO:1) where Xaa represents 4-trans-hydroxyproline.

2. A substantially pure κ-conotoxin peptide consisting of the amino acid sequence Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO:1) where Xaa represents hydroxyproline.

3. A substantially pure κ-conotoxin peptide consisting of the amino acid sequence Cys-Arg-Ile-Xaa-Asn-Gln-Lys-Cys-Phe-Gln-His-Leu-Asp-Asp-Cys-Cys-Ser-Arg-Lys-Cys-Asn-Arg-Phe-Asn-Lys-Cys-Val (SEQ ID NO:1) where Xaa represents proline.

* * * * *